US008366600B2

(12) United States Patent
Sebree et al.

(10) Patent No.: US 8,366,600 B2
(45) Date of Patent: Feb. 5, 2013

(54) POLYAMINE ENHANCED FORMULATIONS FOR TRIPTAN COMPOUND IONTOPHORESIS

(75) Inventors: Terri B. Sebree, Gladwyne, PA (US); Michael Horstmann, Neuwied (DE); Mohammad Sameti, Bonn (DE)

(73) Assignee: NuPathe Inc., Conshohocken, PA (US)

( * ) Notice: Subject to any disclaimer, the term of this patent is extended or adjusted under 35 U.S.C. 154(b) by 306 days.

(21) Appl. No.: 12/214,555

(22) Filed: Jun. 19, 2008

(65) Prior Publication Data
US 2009/0318847 A1    Dec. 24, 2009

(51) Int. Cl.
*B64D 10/00*      (2006.01)
(52) U.S. Cl. .......................... 600/20; 424/449
(58) Field of Classification Search ........................ None
See application file for complete search history.

(56) References Cited

U.S. PATENT DOCUMENTS

| | | | |
|---|---|---|---|
| 4,822,802 A | 4/1989 | Levy et al. | |
| 4,927,408 A | 5/1990 | Haak et al. | |
| 5,207,752 A | 5/1993 | Sorenson et al. | |
| 5,358,483 A | 10/1994 | Sibalis | |
| 5,458,569 A | 10/1995 | Kirk, III et al. | |
| 5,466,217 A | 11/1995 | Myers et al. | |
| 5,533,971 A | 7/1996 | Phipps | |
| 5,605,536 A | 2/1997 | Sibalis | |
| 5,651,768 A | 7/1997 | Sibalis | |
| 5,685,837 A | 11/1997 | Horstmann et al. | |
| 5,697,896 A | 12/1997 | McNichols et al. | |
| 5,807,571 A | 9/1998 | List et al. | |
| 5,882,677 A * | 3/1999 | Kupperblatt | 424/449 |
| 5,941,843 A | 8/1999 | Atanasoska et al. | |
| 6,035,234 A | 3/2000 | Riddle et al. | |
| 6,090,095 A | 7/2000 | McNichols et al. | |
| 6,171,294 B1 | 1/2001 | Southam et al. | |
| 6,216,033 B1 | 4/2001 | Southam et al. | |
| 6,245,347 B1 | 6/2001 | Zhang et al. | |
| 6,416,503 B1 * | 7/2002 | Suzuki et al. | 604/501 |
| 6,421,561 B1 | 7/2002 | Morris | |
| 6,425,892 B2 | 7/2002 | Southam et al. | |
| 6,653,014 B2 | 11/2003 | Anderson et al. | |
| 6,745,071 B1 | 6/2004 | Grace et al. | |
| 6,842,640 B2 | 1/2005 | Riddle et al. | |
| 6,975,902 B2 | 12/2005 | Phipps et al. | |
| 7,018,370 B2 | 3/2006 | Southam et al. | |
| 7,302,293 B2 | 11/2007 | Southam et al. | |
| 2003/0013753 A1 | 1/2003 | Aung-Din | |
| 2003/0124179 A1 | 7/2003 | Jacobsen et al. | |
| 2004/0028721 A1* | 2/2004 | Colombo et al. | 424/443 |
| 2004/0242770 A1 | 12/2004 | Feldstein et al. | |
| 2005/0148996 A1 | 7/2005 | Sun et al. | |
| 2005/0228336 A1 | 10/2005 | Keusch et al. | |
| 2006/0253061 A1 | 11/2006 | Anderson et al. | |
| 2007/0093788 A1 | 4/2007 | Carter | |
| 2007/0093789 A1* | 4/2007 | Smith | 604/890.1 |
| 2011/0111029 A1 | 5/2011 | Schmitz et al. | |

FOREIGN PATENT DOCUMENTS
WO    WO-2007/120747 A2    10/2007

OTHER PUBLICATIONS

Patel et al. In vitro and in vivo evaluation of the transdermal iontophoretic delivery of sumatriptan succinate, European Journal of Pharmaceutics and Biopharmaceuticals 66 (2007) 296-301 (available online Nov. 14, 2006).*
Preservative Directory. Household and Personal Products Industry. Pub. May 1, 2003.*
Clariant Phenonip brochure, available at <http://www.thesoapkitchen.co.uk/-images/MSDS/preservatives/product_info_phenonip.pdf>.*
ALZA Corporation (JNJ) Receives FDA Approval for IONSYS™ (Fentanyl Iontophoretic Transdermal System), retrievied online at http://www.biospace.com/news_story.aspx?NewsEntityId=19447&source=news-email (2006).
Anderson, Carter R. et al., "Effects of Iontophoresis Current Magnitude and Duration of Dexamethasone Deposition and Localized Drug Retention," *Physical Therapy*, vol. 83:161-170 (2003).
Anderson, Carter R. et al., "Quantification of Total Dexamethasone Phosphate Delivery by Iontophoresis," *International Journal of Pharmaceutical Compounding*, vol. 7(2):155-159 (2003).
Banga, Ajay K. et al., "Iontophoretic Delivery of Drugs: Fundamentals, Developments and Biomedical Applications," *Journal of Controlled Release*, vol. 7:1-24 (1988).
Chaturvedula, Ayyappa et al., "Dermal, Subdermal, and Systemic Concentrations of Granisetron by Iontophoretic Delivery," *Pharmaceutical Research*, vol. 22(8):1313-1319 (2005).
Chaturvedula, Ayyappa et al., "In vivo iontophoretic delivery and pharmacokinetics of salmon calcitonin," *International Journal of Pharmaceutics*, vol. 297:190-196 (2005).
Christensen, Michael L. et al., "Pharmacokinetics of Sumatriptan Nasal Spray in Adolescents," *J. Clin. Pharmacol.*, vol. 43:721-726 (2003).
Duquesnoy, C. et al., "Comparative clinical pharmacokinetics of single doses of sumatriptan following subcutaneous, oral, rectal and intranasal administration," *European Journal of Pharmaceutical Sciences*, vol. 6:99-104 (1998).
Femenia-Font, A. et al., "Iontophoretic Transdermal Delivery of Sumatriptan: Effect of Current Density and Ionic Strength," *Journal of PHarmaceutical Sciences*, vol. 94(10):2183-2186 (2005).
Jadoul, Anne et al., "Transdermal Permeation of Alniditan by Iontophoresis: In Vitro Optimization and Human Pharmacokinetic Data," *Pharmaceutical Research*, vol. 13(9):1348-1353 (1996).
Jhee, Stanford S. et al., "Pharmacokinetics and Pharmacokynamics of the Triptan Antimigraine Agents," *Clin. Pharmacokinet.*, vol. 40(3):189-205 (2001).
Kalia, Y. et al., "Transdermal iontophoretic delivery of antimigraine therapeutics in vivo," *2004 AAPS Annual Meeting and Exposition*, (2004).

(Continued)

*Primary Examiner* — David J Blanchard
*Assistant Examiner* — Daniel F Coughlin
(74) *Attorney, Agent, or Firm* — McCarter & English, LLP

(57) ABSTRACT

A patch and compositions for iontophoresis of triptan compounds are described.

27 Claims, No Drawings

OTHER PUBLICATIONS

Lattin, Gary A. et al., "Electronic Control of Iontophoretic Drug Delivery," *Annals of the New Yorker Academy of Sciences*, vol. 618:450-464 (1991).

Patel, Sonal R. et al., "In vitro and in vivo evaluation of the transdermal iontophoretic delivery of sumatriptan succinate," *European Journal of Pharmaceutics and Biopharmaceutics*, vol. 66:296-301 (2007).

Patel, Sonal R. et al., "Transdermal iontophoresis of sumatriptan succinate in vitro," *205th Meeting, The Electrochemical Society, Inc.*, Abs. 725 (2004).

Patel, S.R. et al., "Transdermal iontophoretic delivery of sumatriptan in vitro," Cephalalgia, Abstracts of the 15th Migraine Trust International Symposium, (2004).

Pierce, M. et al., "NP101: A Novel Formulation of Sumatriptan Succinate Utilizing SmartRelief™ Transdermal Technology," *50th Annual Meeting American Headache Society*, p. S46, No. S17 (2008).

Scholpp, J. et al., "Early treatment of a migraine attack while pain is still mild increases the efficacy of sumatriptan," *Cephalalgia*, vol. 24:925-933 (2004).

Siegel, Steven J. et al., "A Unique Iontophoretic Patch for Optimal Transdermal Delivery of Sumatriptan," *Pharmaceutical Research*, vol. 24(10):1919-1926 (2007).

Vyteris Announces Positive Results for Phase I Clinical Trial, *Vyteris Holdings (Nevada)*, Inc. (2005).

Vyteris, "The smart patch by vyteris, The future of drug delivery. . . today!" JP Morgan 25th Annual Healthcare Conference (Jan. 2007).

Xu, Xiaohui et al., "Determination of degradation products of sumatriptan succinate using LC-MS and LC-MS-MS," *Journal of Pharmaceutical and Biomedical Analysis*, vol. 26:367-377 (2001).

International Search Report and Written Opinion for No. PCT/US07/09000.

International Preliminary Examination Report for Application No. PCT/US08/81837, dated Jan. 30, 2009.

International Preliminary Examination Report for Application No. PCT/US08/81841, dated Jan. 22, 2009.

Office Action from U.S. Appl. No. 12/737,209, dated May 8, 2012.

Response filed in U.S. Appl. No. 12/737,209, dated Sep. 7, 2012.

\* cited by examiner

POLYAMINE ENHANCED FORMULATIONS FOR TRIPTAN COMPOUND IONTOPHORESIS

BACKGROUND

The process of iontophoresis was described by LeDuc in 1908 and has since found commercial use in the delivery of ionically charged therapeutic agent molecules such as pilocarpine, lidocaine and dexamethasone. In this delivery method, ions bearing a positive charge are driven across the skin at the site of an electrolytic electrical system anode while ions bearing a negative charge are driven across the skin at the site of an electrolytic system cathode.

Earlier, and some present, iontophoretic devices have been typically constructed of two electrodes attached by adhesive materials to a patient, each connected by a wire to a remote power supply, generally a microprocessor-controlled electrical instrument.

A recent publication has indicated that Sumatriptan can be transdermally transported effectively using iontophoresis (Femenia-Font et al, J. Pharm Sci 94, 2183-2186, 2005). In this study, iontophoretic transport of Sumatriptan was found to be at a rate 385 fold higher than passive transport.

Another recent study has concluded that iontophoresis can be useful in the delivery of anti-migraine compounds. In this study, a two-component system comprised of an electronic controller connected by wire to a transdermal patch was used to deliver Zolmatriptan. The company presenting the results from this study has concluded that programmable capability of its iontophoresis units may allow rapid initial delivery for fast action, while a sustained, low level maintenance dose can be utilized for a prevention of headache recurrence. A significant limitation of this device lies in the two-component structure of the delivery system; the wire connections between the controller and patches are a nuisance to the wearer. Additionally, programmable controllers can be expensive if utilized on a single use basis, or lost, contaminated, broken, etc. if used on a reusable basis.

SUMMARY

The invention is based, at least in part, on the surprising discovery that the use of polyamines in formulations for iontophoresis allows for the administration of much higher dosages of therapeutic agents through the use of higher amounts of electricity, without causing a subject substantial amounts of skin irritation. For example, the polyamine formulations of the invention allowed for the use of up to 4 mA of current without causing significant erythema to the subjects using the patches.

In one embodiment, the invention pertains, at least in part, to an iontophoretic transdermal patch for the delivery of a triptan compound or a salt thereof. The patch comprises an anode reservoir, a cathode reservoir and appropriate electrical circuitry. Furthermore, at least one of the reservoirs comprises a mixture comprises of a polyamine hydrogel, water, a triptan compound or salt thereof, and optionally one or more additives.

In a further embodiment, the invention also pertains to iontophoretic patches wherein the anode reservoir comprises: approximately 3.0% to about 5.0% sumatriptan succinate; approximately 84% to about 88% water; approximately 4.0% to about 7.0% alkylated methacrylate co-polymer; approximately 1.0% to about 6.0% fatty acids (e.g., about 1.0% to about 5.0% lauric acid and about approximately 0.05% to about 0.75% adipic acid); and approximately 0.05% to about 0.75% methyl para-hydroxy benzoate.

In another further embodiment, the invention also features iontophoretic transdermal patches wherein the cathode reservoir comprises: approximately 95% to about 98% water; approximately 1.0% to about 3.0% hydroxypropylcellulose; approximately 0.5% to about 1.5% salt; and approximately 0.05% to about 0.75% methyl para-hydroxy benzoate.

The invention also pertains, at least in part, to methods of treating (e.g., for a triptan compound responsive state, e.g., migraine) a subject, by administering an effective amount of a triptan compound or a salt thereof to a subject using an iontophoretic transdermal patch as described herein.

DETAILED DESCRIPTION

1. Iontophoretic Patches of the Invention

The invention pertains, at least in part, to an integrated iontophoretic transdermal patch for the delivery of a triptan compound or a salt thereof.

The term "iontophoretic transdermal patch" includes integrated devices which allow for the administration of triptan compounds through the skin by using electrical current to promote the absorption of the drug from the patch through the skin of the subject. In one embodiment, the patch comprises electrical components, the triptan compound, and an adhesive backing layer.

In an embodiment, the invention pertains, at least in part, to an iontophoretic transdermal patch for the delivery of a triptan compound or a salt thereof. The patch comprises an anode reservoir, a cathode reservoir and appropriate electrical circuitry. Furthermore, at least one of the reservoirs comprises a polyamine and a mixture comprises of a water, a triptan compound or salt thereof, and optionally one or more additives, such as, but not limited to a solubility enhancer, a permeation enhancer, a preservative and/or a antimicrobial agent.

The term "polyamine" particularly includes cationic organic compounds having at least two positively charged groups, preferably amino groups selected from the group comprising primary amino groups, secondary amino groups and tertiary amino groups. The invention also includes polyamines comprising, for instance, pyrrolidino, piperidino or morpholino groups. Generally, the polyamines used in accordance with the present invention preferably include polyelectrolytes which are polymers or macromolecules comprising two or more positive charges upon being dissolved in water or an aqueous solvent.

In a further embodiment, the term "polyamine" include organic compounds having two or more primary amino groups. Examples include putrescine, cadaverine, spermidine, and spermine. Other polyamines include cyclen and other cyclic polyamines. Examples of polymer polyamines include those based on the aziridine monomer, such as polyethylene amine.

According to one embodiment of the invention, the polyamine may selected from the group comprising acrylate copolymers, methacrylate copolymers, alkylated acrylate copolymers and alkylated methacrylate copolymers. These copolymers contain two or more amino groups as defined above.

The alkyl group may selected from $C_1$ to $C_{12}$ alkyl groups (linear or branched), such as, for instance, methyl, ethyl, propyl, isopropyl, or butyl. The alkylated copolymers may also include hydroxylated alkyl groups, preferably $C_1$ to $C_{12}$ hydroxyalkyl groups, such as, for instance, hydroxymethyl, hydroxyethyl or hydroxypropyl. Concerning the polyamines, an example of an amino group is the "diamino ethyl" moiety present within an organic compound, optionally within a polymeric organic compound.

Other examples of polymeric polyamines of the invention include, but are not limited to, methacrylate copolymers such as copolymers of butylated or/and methylated methacrylate(s) and dimethyl aminoethyl methacrylate. Other examples of copolymers include the "basic butylated methacrylate copolymer" described in the Pharmacopoea Europaea (Ph. Eur.), the "amino methacrylate copolymer" described in the USP/NF, and the "aminoalkyl methacrylate copolymer E" described in "Japanese Pharmaceutical Excipients". Such copolymers are commercially available under the trademark Eudragit® (from Evonik Industries, formerly Degussa), for instance, Eudragit® RL 100, Eudragit® RL PQ, Eudragit® RS 100, Eudragit® RS PQ, and Eudragit® E 100.

EUDRAGIT® E 100 is a cationic copolymer based on dimethylaminoethyl methacrylate, butylmethacrylate, and methyl methacrylate. The average molecular weight of this polymer is approximately 150,000.

Generally, any polyamines containing at least two amino groups as defined above may be used in the compositions of the present invention, provided that they are toxicologically safe and suitable for use in pharmaceutical products. Polyamines useful for producing the compositions of the present invention may further be selected from the group comprising cyclic and macrocyclic polyamines, such as cyclen, polyamines based on the aziridine monomer, such as polyethylene imines, as well as polyethylene amines, putrescine, cadaverine, spermidine, spermine, as well as polypropyleneimine, polyvinylamine, polyvinylimine, polyvinylimidazol, polyvinylpyridine, and polyguanidines. In one embodiment, the polyamine compounds of the present invention have a molecular mass of 1500 or above.

In a further embodiment, the composition of the present invention comprises a combination of at least two different polyamine compounds selected from the polyamine compounds defined above.

The polyamine compounds to be used in accordance with the compositions of the invention are present in the form of polyamine salts, particularly water-soluble polyamine salts. Suitable salts are obtainable by combining or reacting the above-mentioned polyamines with suitable acids, preferably organic acids, by standard procedures.

In one embodiment, the proportion of said polyamine(s) or polyamine salt(s) is in the range of about 1 to about 25%-wt., about 5 to about 20%-wt., or about 10 to about 18%-wt., relative to the total weight of the composition.

In a further embodiment, a anode reservoir may comprise between about 3.0% to about 10.0%, between about 4.0% and about 9.0%, between about 5.0% and about 8.0%, between about 5.0% and about 6.0%, or about 5.86% alkylated methacrylate co polymer, e.g., butylated methacrylate copolymer, e.g., Eudragit E100.

In further embodiments of the present invention, the composition further comprises at least one acid selected from the group comprising fatty acids and dicarboxylic acids. However, other types of organic acids may also be used, as, for instance, acids selected from hydroxy alkanoic acids or from tricarboxylic acids.

By combining the above-discussed polyamine(s), e.g. amino group-containing polyacrylate copolymers, with one or more acids selected from the group of fatty acids and dicarboxylic acids, the corresponding polyamine salts are obtained. These polyamine salts are generally water-soluble and, upon dissolution in water, form a polymeric electrolyte.

Furthermore, the present compositions comprising said polyamine salts have been found to be particularly suitable as a carrier or reservoir for ionic, dissociated active agents in iontophoretic devices.

Further, it was found that by combining polyamine(s) with one or more of said acids in the presence of water, hydrogels can easily be obtained which are particular useful to serve as reservoir compositions in iontophoretic systems.

The term "fatty acids" includes aliphatic monocarboxylic acids having an aliphatic tail comprising up to 30 C atoms, which acids may be linear or branched, saturated or unsaturated. Preferably, $C_6$ to $C_{14}$ saturated fatty acids are used. Fatty acids that may be used in accordance with the present invention include, for instance, hexanoic acid, decanoic acid, lauric acid, myristic acid, palmitic acid, caprylic acid and stearic acid.

The term "dicarboxylic acid" includes organic compounds that are substituted with two carboxylic acid functional groups, which compounds include linear, branched and cyclic compounds, which compounds may be saturated or unsaturated. For instance, the dicarboxylic acid may be selected from dicarboxylic fatty acids, particularly from $C_4$ to $C_{10}$ dicarboxylic acids. Examples of fatty dicarboxylic acids include glutaric acid, adipic acid and pimelic acid.

In further embodiments, the composition may contain a combination comprising at least two fatty acids, or a combination comprising at least two dicarboxylic acids, or a combination comprising at least one fatty acid and at least one dicarboxylic acid.

Generally, the amount of fatty acid(s) or/and dicarboxylic acid(s) is adjusted so as to be at least sufficient to solubilize the polyamine(s), and/or other components present in the composition(s), in order to obtain a hydrogel composition having one or more properties, such as, for example, semisolid or solid consistency as well as skin-adhesive properties.

Preferably, the total amount of fatty acid(s) or/and dicarboxylic acid(s) in the composition is in the range of 0.1 to 15%-wt., particularly in the range of 0.5 to 10%-wt. According to a further embodiment, the concentration of the fatty acid(s) may be about 0.1 to 10%-wt, preferably 0.5 to 7.0%-wt. According to another further embodiment, the concentration of the dicarboxylic acid(s) may be about 0.05 to 5%-wt., or about 0.1 to 2.0%-wt.

The compositions of the invention may be formulated as hydrogels which including at least one gel-forming polymer (e.g. a polyamine or a salt thereof as described above, and/or other gel-forming polymers as generally known in the field of pharmaceutical preparations), together with a gel-forming amount of water or aqueous solvent mixture.

The relative amounts of water and gel-forming components may be adjusted so as to obtain a hydrogel having solid or semi-solid consistency. However, the formulations of the present invention may also be formulated as liquids.

In a further embodiment, the hydrogel compositions may comprise additional gel-forming polymers which may be selected e.g. from the group consisting of polyacrylates or cellulose derivatives such as hydroxypropylmethyl cellulose, hydroxypropyl cellulose or hydroxyethyl cellulose.

The ionic strength can be adjusted by varying the proportion of water within the hydrogel. Thus, the ionic strength can be adjusted to optimize the efficacy of the iontophoretic process in each particular case.

The term "triptan compound" includes triptan compounds, derivatives and salts. The term also includes compounds that contain a 2-(1H-indol-3-yl)-N,N-dimethylethanamine moiety. Examples of triptan compounds include, but are not limited to, almotriptan, frovatriptan, eletriptan, zolmitriptan, rizatriptan, sumatriptan, naratriptan, and pharmaceutically acceptable salts thereof.

Examples of triptan compounds that may be used in the methods of the invention include those listed in Table 1. The concentrations of the triptan compound in the plasma to maintain an effective amount will vary with the compound used. In the case of Sumatriptan, an initial plasma concentration of 15-20 ng/mL may generally be effective. However, an initial concentration between 20 and 25, possibly 22.5 ng/mL, may be desired.

Table I shows additional triptan pharmacokinetics where $C_{max}$ is the expected maximum concentration in the patient's plasma and AUC is the total plasma concentration.

TABLE I

Triptan Pharmacokinetics

| Drug | $C_{max}$ ng/mL | AUC ng · hr/mL |
|---|---|---|
| Almotriptan | 52 | 310 |
| Frovatriptan | 5 | 45 |
| Eletriptan | 200 | 1,300 |
| Naratriptan | 8 | 75 |
| Rizatriptan | 22 | 78 |
| Zolmitriptan | 4 | 20 |

Examples of pharmaceutically acceptable salts of triptan compounds which may be used in the methods and patches of the invention include, but are not limited to, chloride, bromide, iodide, sulfuric, phosphate, lactate, citrate, tartarate, salicylate, succinate, maleate, gluconate, mesylate, laurate, dodecylate, myristate, palmitate, stearate, coconoate, behinate, oleate, linoleate, linolenate, eicosapentaenoate, eicosahexaenoate, docosapentaenoate, docosahexaenoate, eicosanoids and the like. In a further embodiment, the triptan compound is sumatriptan succinate. In certain embodiments, the salt of the triptan compound may be selected such that it does not react with the other components of the patch, such as the metal electrode. In certain embodiments, the salt may be selected such that it does not form a significant amount of an insoluble residue when in contact with the metal components of the patch of the invention.

In one embodiment, the reservoir includes a mixture that includes between about 0.1% and about 20%, between about 0.2% and about 10%, between about 2% and about 10%, between about 3% and about 5% triptan, or between about 0.1% and about 0.5% of a triptan, e.g., sumatriptan.

The reservoirs may be comprised of a hydrogel into which the sumatriptan solution may be absorbed. The hydrogel may or may not be substantially cross linked. The hydrogel may be comprised of one or more polymers. Examples of such polymers that the hydrogel may be based upon include polyacrylates, polyisobutylene, cellulose derivatives, polyisoprene, styrene-polybutylene-styrene block copolymers, polysiloxanes, polyurethanes, and combinations thereof.

In a further embodiment, an ion compensator is added to the formulation to enhance solubility of the hydrogel by, for example, compensating for the missing hydrophilic ions.

In one embodiment, the ion compensator is adipic acid. In one embodiment, the formulation comprises an effective amount of a fatty acid, e.g., an amount sufficient to solubilize the hydrogel or polyamine such that the patch performs its intended function. The fatty acid may be a dicarboxylic fatty acid, e.g., a $C_4$-$C_{10}$ dicarboxylic acid. Examples of fatty dicarboxylic acids include glutaric, adipic and pimelic acids. In another embodiment, the patch comprises between about 0.1% and about 1.0%, between about 0.15% and about 0.5% or between about 0.20% and about 0.40% adipic acid.

In a further embodiment, the reservoir may comprise a hydrogel or a liquid aqueous composition which comprises an alkylated methacrylate polyamine copolymer, between 0.5 and 10%-wt. of at least one triptan or salt thereof, between 0.02 and 0.5%-wt. methyl para-hydroxybenzoate, between about 1.0 and 5.0%-wt. lauric acid, and between about 0.05 and 0.75%-wt. adipic acid, and said hydrogel composition has a water content of at least 80%-wt.

In a further embodiment, the reservoir may comprise a hydrogel or a liquid aqueous composition which comprises 4 to 7%-wt. alkylated methacrylate polyamine copolymer, 3 to 5%-wt. of at least one triptan compound or salt thereof, 1 to 5%-wt. lauric acid, 0.05 to 0.75%-wt. adipic acid, 0.05 to 0.75%-wt. methyl para-hydroxybenzoate, 84 to 88%-wt. water.

In a further embodiment, the reservoir may comprise about 4.00%-wt. of triptan compound, 86.37%-wt. of water, 5.86%-wt. of alkylated methacrylate copolymer (=polyamine), 3.40%-wt. of lauric acid, 0.27%-wt. of adipic acid, and 0.10%-wt. of methyl para-hydroxybenzoate, wherein each specified value may vary by ±10% relative to the indicated mean value.

In one embodiment, the reservoirs each have a surface area of about 1 cm$^3$, about 2 cm$^3$, about 3 cm$^3$, about 4 cm$^3$, about 5 cm$^3$, about 6 cm$^3$, about 7 cm$^3$, about 8 cm$^3$, about 9 cm$^3$, about 10 cm$^3$, about 11 cm$^3$, about 12 cm$^3$, about 13 cm$^3$, about 14 cm$^3$, about 15 cm$^3$, about 16 cm$^3$, about 17 cm$^3$, about 18 cm$^3$, about 19 cm$^3$, about 20 cm$^3$, about 21 cm$^3$, about 22 cm$^3$, about 23 cm$^3$, about 24 cm$^3$, about 25 cm$^3$, about 26 cm$^3$, about 27 cm$^3$, about 28 cm$^3$, about 29 cm$^3$, about 30 cm$^3$, about 31 cm$^3$, about 32 cm$^3$, about 33 cm$^3$, about 34 cm$^3$, about 35 cm$^3$, about 36 cm$^3$, about 37 cm$^3$, about 38 cm$^3$, about 39 cm$^3$, about 40 cm$^3$, about 41 cm$^3$, about 42 cm$^3$, about 43 cm$^3$, about 44 cm$^3$, about 45 cm$^3$, about 46 cm$^3$, about 47 cm$^3$, about 48 cm$^3$, about 49 cm$^3$, or about 50 cm$^3$ or greater.

In a further embodiment, the reservoir is self-adhesive. The reservoir may also contain an additional tackifier, such as, but not limited to, hydrocarbon resins, rosin derivatives, glycols (e.g., glycerol, 1,3 butanediol, propylene glycol, polyethylene glycol), and succinic acid.

The term "solubility enhancer" includes compounds which increase the solubility of the triptan compound in its vehicle. This can be achieved, for example, either through changing triptan compound-vehicle interaction by introducing different excipients, or through changing the crystallinity of the triptan compound. Examples of solubility enhancers include water diols, such as propylene glycol and glycerol; monoalcohols, such as ethanol, propanol, and higher alcohols; DMSO; dimethylformamide; N,N-dimethylacetamide; 2-pyrrolidone; N-(2-hydroxyethyl)pyrrolidone, N-methylpyrrolidone, 1-dodecylazacycloheptan-2-one and other n-substituted-alkyl-azacycloalkyl-2-ones.

The term "permeation enhancer" includes compounds which increase the permeability of skin to the triptan compound, i.e., so as to increase the rate at which the triptan compound permeates through the skin and enters the bloodstream. The enhanced permeation effected through the use of such enhancers can be observed, for example, by measuring the rate of diffusion of the triptan compound through animal or human skin using a diffusion cell apparatus.

Examples of permeation enhancers include, but are not limited to, dimethylsulfoxide (DMSO), N,N-dimethylacetamide (DMA), decylmethylsulfoxide (Clo MSO), polyethylene glycol monolaurate (PEGML), propylene glycol (PG), PGML, glycerol monolaurate (GML), lecithin, the 1-substituted azacycloheptan-2-ones, particularly 1-n-dodecylcyclazacycloheptan-2-one, alcohols, and the like. The permeation enhancer may also be a vegetable oil such as, for example, safflower oil, cotton seed oil and corn oil.

In addition, other agents may be used to enhance the solubility of the polyamines. Examples of such solubilizing agents include, but are not limited to, fatty acids, e.g., $C_6$-$C_{14}$ saturated fatty acids. Examples of saturated fatty acids include hexanoic, decanoic, myristic, palmitic, lauric and caprylic acids. In a further embodiment, the fatty acid is lauric acid and is present in amounts between about 0.1% and about 10%, between about 0.2% and about 9.5%, between about 0.3% and about 9.0%, between about 0.4% and about 8.5%, between about 0.5% and about 8.0%, between about 1.0% and about 7.0%, between about 1.5% and about 6.0%, between about 2.0% and about 5.0%, between about 3.0% and about 4.0% and about 3.40%.

The term "antimicrobial agent" includes agents which prevent the growth of microbials in the patch. Examples of antimicrobials include, but are not limited to, salts of chlorhexidine, such as iodopropynyl butylcarbamate, diazolidinyl urea, chlorhexidene digluconate, chlorhexidene acetate, chlorhexidene isethionate, and chlorhexidene hydrochloride. Other cationic antimicrobial agents may also be used, such as benzalkonium chloride, benzethonium chloride, triclocarbon, polyhexamethylene biguanide, cetylpyridium chloride, methyl and benzothonium chloride. Other antimicrobial agents include, but are not limited to: halogenated phenolic compounds, such as 2,4,4',-trichloro-2-hydroxy diphenyl ether (Triclosan); parachlorometa xylenol (PCMX); and short chain alcohols, such as ethanol, propanol, and the like. Other examples of antimicrobial agents include methyl para-hydroxybenzoate or methyl 4-hydroxy benzoate.

In a further embodiment, the compositions of the invention comprise between about 0.01% and about 1.0%, between about 0.05% and about 0.5%, between about 0.07% and about 0.4%, between about 0.08% and about 0.3%, between about 0.09% and about 0.2%, and about 0.10% methyl para-hydroxybenzoate.

In a further embodiment, the solution has a pH of about 3 to about 8, about 5.5 to about 7, or about 6. In another further embodiment, the pH of solution is selected such that usage of the patch does not substantially affect the pH of the skin. In a further embodiment, the pH of the skin changes about ±4.0 or less, about ±3.5 or less, about ±3.0 or less, about ±2.5 or less, about ±2.0 or less, about ±1.5 or less, about ±1.0 or less, or about ±0.5 of less.

The backing layer can be any material known in the art for being suitable for such purposes. The backing layer is preferably flexible and suitable materials include without limitation, cellophane, cellulose acetate, ethylcellulose, plasticized vinylacetate-vinylchloride coploymers, polyethylene terephthalate, nylon, polyethylene, polypropylene, polyvinylidene chloride, coated flexible fibrous backings such as paper and cloth and aluminum foil. The adhesive material may be any material known in the art which is suitable for use in the iontophoretic patches of the invention.

In a further embodiment, the patch comprises an electrode which does not significantly react with the triptan compound or anti-migraine compound to form an insoluble salt. In a further embodiment, the electrode is comprised of a metal with a reactivity similar to zinc. In another further embodiment, the electrode includes silver, iron, aluminum, tin, copper, zinc, nickel, brass, metal alloys, conductive polymers, or coatings or mixtures thereof.

In a further embodiment, the electrical circuitry of the patch comprises a battery which operates throughout use of the patch. In a further embodiment, the battery is integrated into the patch and may be the main, if not sole, source of power of the patch.

The invention also includes embodiments in which said composition or the device of the invention further comprises an adsorbent material that is soaked or impregnated with said composition which is generally a liquid aqueous composition or hydrogel composition.

The adsorbent material which is soaked or impregnated with the aqueous or hydrogel composition(s) serves to keep said composition in place and, at the same time, to maintain the low-viscosity structure. Suitable adsorbent materials may be selected from fibrous pads, fabrics, sponges, tissues, nonwoven or woven materials, felts or felt-like materials, etc.

According to a further embodiment, the composition and/or patch of the present invention has adhesive properties, to ensure that the composition is maintained in direct and complete contact with the skin at the site of application during the whole time period of transdermal drug administration. Adhesiveness can be obtained by incorporating one or more adhesive polymers into said compositions. Adhesive polymers suitable for this purpose are generally known to the skilled person. In one embodiment, a polyamine or polyamine salt having adhesive properties is used as said adhesive polymer(s)

In a further embodiment, the compositions and/or patches of the invention are self-adhesive. To render the compositions and/or patches self-adhesive, they may further contain one or more additives selected from the group of tackifiers which group includes, but is not limited to, hydrocarbon resins, rosin derivatives, glycols (such as glycerol, 1,3-butanediol, propylene glycol, polyethylene glycol), and succinic acid.

In yet another embodiment of the invention, the invention pertains to an iontophoretic transdermal patch for the delivery of a sumatriptan or a salt thereof, which comprises an anode reservoir, a cathode reservoir and appropriate electrical circuitry and a polyamine. In a further embodiment, the anode reservoir comprises: approximately 3.0% to about 5.0% sumatriptan succinate (advantageously about 4.00%±10%); approximately 84% to about 88% water (advantageously about 86.37%±10%); approximately 4.0% to about 7.0% alkylated methacrylate co-polymer (advantageously about 5.86%±10%); approximately 1.0% to about 5.0% lauric acid (advantageously about 3.40%±10%); approximately 0.05% to about 0.75% adipic acid (advantageously about 0.27%±10%); and approximately 0.05% to about 0.75% methyl para-hydroxy benzoate (advantageously about 0.10%±10%).

Generally, the compositions of the present invention can be manufactured by conventional methods. The compositions of the present invention are obtainable by dissolving or dispersing the various ingredients (i.e. triptan compound, polyamine, additives) in water or an aqueous solvent mixture. The resulting mixture may then be spread on a flat surface or poured into moulds or extruded, and then allowed to solidify to obtain hydrogel compositions having the desired shape. During these process steps, or after solidification, the composition may be combined with additional components as required to produce the final product, generally a pharmaceutical administration form.

However, various alternative methods for manufacturing the compositions of the present invention may be used, as will be readily realized by the skilled person.

The present invention further encompasses the use of the above-described composition(s) as an integral component of a transdermal patch. Preferably, such composition is incorporated into said patch during manufacture, to form the active substance reservoir of the patch. Further, the present invention encompasses the use of the above-described composition(s) as an integral component of an iontophoretic patch, for example, as an anodic reservoir of the patch. Such composition may be incorporated into the iontophoretic patch during manufacture, to form the anodic reservoir of the patch. The above-mentioned administration forms are obtainable by manufacturing methods generally known in the art.

2. Methods of Treating Subjects Using the Patches of the Invention

In an embodiment, the invention pertains to a method for treating a subject for a triptan compound responsive state, by administering to a subject a steady state concentration of a triptan compound for at least one hour, wherein the compound is not administered intravenously. In a further embodiment, the compound is administered via an iontophoretic patch.

In one embodiment, the patch of the invention allows for the delivery of an effective amount of a triptan compound to a subject in less than about two hours, less than about 90 minutes, less than about one hour, less than about 45 minutes, less than about 30 minutes or less than about 20 minutes.

The term "subject" includes living organisms capable of having triptan compound responsive states (e.g., mammals). Examples of subjects include humans, dogs, cats, horses, cows, goats, rats and mice. In one embodiment, the subject is a human. In a further embodiment, the term includes subjects suffering from a triptan compound responsive state.

The term "effective amount" includes the amount of the triptan compound which is effective to treat a particular triptan compound responsive state.

In one embodiment, the particular triptan compound is sumatriptan and the effective amount is effective to treat a migraine. In this case, the effective amount of sumatriptan may be a concentration of about 10 ng/mL or greater, about 11 ng/mL or greater, about 12 ng/mL or greater, about 13 ng/mL or greater, about 14 ng/mL or greater, about 15 ng/mL or greater, about 16 ng/mL or greater, about 17 ng/mL or greater, about 18 ng/mL or greater, about 19 ng/mL or greater, about 20 ng/mL or greater, about 21 ng/mL or greater, about 22 ng/mL or greater, or about 22.5 ng/mL or greater in said subject's plasma. In another embodiment, the effective amount of sumatriptan delivered systemically is greater than about 5 mg, greater than about 10 mg, or greater than about 15 mg.

The term "treat" includes the reduction or amelioration of one or more symptoms of a triptan compound responsive state. It also may include the prevention of the occurrence or reoccurrence of a triptan compound responsive state.

The term "triptan compound responsive states" includes almotriptan responsive states, zolmitriptan responsive states, rizatriptan responsive states, sumatriptan responsive states, and naratriptan responsive states. The term also includes migraines, familiar hemiplegic migraines (with and without aura), chronic paroxysmal headaches, cluster headaches, migraine headaches, basilar migraines, and atypical headaches accompanied by autonomic symptoms. In certain embodiments, the triptan compound responsive state is a migraine.

The term "delivery" includes the transport of the triptan compound from the patch to the plasma of a subject. In certain embodiments, approximately 1%-30% (or higher) of the triptan compound in the patch is delivered to the plasma of the subject over the course of treatment. The term "systemic delivery" includes delivery to a subject through non-oral administration. Preferred systemic administration methods include transdermal administration.

In an embodiment, the invention pertains to an iontophoretic transdermal patch for the delivery of a triptan compound, e.g., sumatriptan or a salt thereof, wherein the patch allows for the systemic delivery of an effective amount of sumatriptan or a salt thereof to a subject.

The term "delivery time" includes the period of time which the patch is functioning by actively delivering the triptan compound to the subject iontophoretically.

In another embodiment, the patch is able to maintain a steady state concentration of the triptan compound in the subject's plasma for at least one hour, for at least two hours, for at least three hours, for at least four hours, or for at least five hours or more.

In yet a further embodiment, the patch allows for the delivery of an effective amount of sumatriptan in less than about one hour. In another further embodiment, the patch maintains a steady state concentration for at least two hours.

The language "maintain a steady state concentration" refers to the maintenance of a particular concentration (e.g., a desired concentration, e.g., an effective amount) for a particular length of time. In one embodiment, the concentration of the triptan compound in the subject's plasma fluctuates from the average concentration by about 10 ng/ml or less, about 9 ng/ml or less, about 8 ng/ml or less, about 7 ng/ml or less, about 6 ng/ml or less, about 5 ng/ml or less, about 4 ng./ml or less, about 3 ng/ml or less, about 2 ng/ml or less, about 1 ng/ml or less, or by about 0.5 ng/ml or less.

The invention also pertains to a method for treating a subject, by transdermally administering to the subject an effective amount of a triptan compound in less than one hour using an integrated iontophoretic patch. In this embodiment, the patch uses a current density selected such that the current does not substantially irritate the subject's skin. The patch may use an average current density of 0.25 mA/cm$^2$ or less for a significant portion of the delivery time of the triptan compound.

The patch may employ a current which is effective to deliver the amount of the triptan compound needed to treat the triptan compound state of the invention. In one embodiment, the patch is uses a current greater than about 0.5 mA, greater than about 1 mA, greater than about 2 mA, greater than about 3 mA, greater than about 4 mA, or greater than about 5 mA, without substantially irritating a subject's skin. In one embodiment, the patch employs a current of about 4 mA for about an hour.

In another embodiment, the patch delivers about 100 mAmin or greater, 200 mA min or greater, about 300 mA min or greater, about 400 mAmin or greater, about 500 mA min or greater, about 600 mA min or greater or about 700 mA min or greater of current with out substantially irritating a subject's skin.

The term "significant portion" includes at least 30% of the delivery time or more, at least 40% of the delivery time or more, at least 50% of the delivery time or more, at least 60% of the delivery time or more, at least 70% of the delivery time or more, at least 75% of the delivery time or more, at least 80% of the delivery time or more, at least 85% of the delivery time or more, at least 90% of the delivery time or more, or at least 95% of the delivery time or more.

The language "does not substantially irritate a subject's skin" includes patches which result in a skin erythema score of 2.50 or less, 2.00 or less, or 1.00 or less about two hours, 24 hours, two days, three days, four days or one week after patch removal. In another further embodiment, the language "does not substantially irritate a subject's skin" includes patches which result in a skin erythema score of 2.50 or less, 2.00 or less, or 1.00 or less immediately after patch removal. In another further embodiment, the patches of the invention do not cause punctuate lesions when used according to the methods of the invention.

In another further embodiment, the invention also pertains to a method for treating a triptan compound responsive state in a subject. The method includes administering transdermally to the subject an effective steady state concentration of a triptan compound using an integrated patch. In a further embodiment, the effective concentration is at least 20 ng/mL.

In another embodiment, the invention also pertains, at least in part, to a method for treating a subject for a sumatriptan responsive state. The method includes transdermally administering to the subject an effective amount (e.g., about 5 mg or greater, or about 10 mg or greater) of sumatriptan or a salt thereof, such that the subject is treated. The transdermal administration may include the use of a iontophoretic patch.

The term "transdermal" includes delivery methods which occur through the skin of a subject without puncturing the subject's skin.

EXEMPLIFICATION OF THE INVENTION

Example 1

Use of Iontophoretic Patches to Deliver Sumatriptan Succinate

A single center, open label, single-dose, five period study was conducted to compare the pharmacokinetics of four prototypes of sumatriptan iontophoretic transdermal patches of the invention with 100 mg oral sumatriptan succinate in healthy volunteers. Subjects, at minimum, participated in Treatment A and Treatment B.

The iontophoretic patches used were self-contained, with an external power source, designed to be applied to the surface of the skin and to deliver medication systemically.

The patch treatments and prototype iontophoretic patches prepared for this example, are detailed in Table 2 below.

The patches for Treatments A and C were applied to a clean, dry, relatively hair free area of the upper arm. Treatments were applied to alternating arms. The patches for Treatments D and E were applied to a clean, dry, relatively hair free area of the upper back. Treatments were applied to alternating right and left positions on the upper back. PK blood samples were scheduled for collection per subject for each of the five periods.

Iontophoretic delivery system assessments including adhesion and dermal irritation and the amount of adhesive residue on the skin were performed during Treatments A, C, D and E.

The subjects were healthy adult volunteers (four males and five females) who were willing to attend the clinic for five treatment periods. The subjects received no other medication (prescription or over-the-counter) for two weeks prior to study entry, unless approved by the designated physician. Study participants were between 19 and 50 years old. The mean age was 28 years old.

The five treatments, as described in Table 2, were administered in five clinical periods. Four of the five dosing treatments were using the patches comprising the formulations of the invention. The patch was applied to the upper arm or upper back depending on the Treatment period.

In treatment B, the subjects received an Imigran FTab oral tablet (100 mg sumatriptan succinate) with 240 mL of water after an overnight fast. Subjects remained fasted for 4 hours after dosing.

The drug reservoir pad (anode) formulation for Treatment A, C, D and E was: 10% polyamine formulation plus 4% sumatriptan succinate (loaded with up to 120 mg of sumatriptan).

The salt reservoir pad (cathode) formulation for Treatments A, C, D and E was: • 2% hydroxypropylcellulose (HPC) and NaCl.

There were no serious adverse events reported during the study periods. The most frequently reported adverse event was headache related to treatment B (sumatriptan succinate 100 mg oral tablet) and tingling and itching at patch site for patch treatments A, C, D and E.

TABLE 2

Iontophoretic Patch Dosing Treatments

| Period | Treatment | Placement | Wear Time(hr) | Waveform | Theoretical Delivery Dose | mA Minutes | Anode Electrode Size |
|---|---|---|---|---|---|---|---|
| 1 | A | Upper arm | 6 | 3 mA 1.0 hr then 1.5 mA for 5.0 hrs | 3 mg/hr × 1 hr + 1.5 mg/hr × 5 hrs = 10.5 mg | 630 | 5 cm² |
| 3 | C | Upper arm | 6 | 3 mA 1.0 hr then 1.5 mA for 5.0 hrs | 3 mg/hr × 1 hr + 1.5 mg/hr × 5 hrs = 10.5 mg | 630 | 5 cm² |
| 4 | D | Upper back | 6 | 4 mA 1.0 hr then 2.0 mA for 5.0 hrs | 4 mg/hr × 1 hr + 2 mg/hr × 5 hr = 14.0 mg | 840 | 10 cm² |
| 5 | E | Upper back | 4 | 4 mA 1.0 hr then 2.0 mA for 3.0 hrs | 4 mg/hr × 1 hr + 2 mg/hr × 3 hr = 10.0 mg | 600 | 10 cm² |

Nine subjects participated in Treatment B a 100 mg sumatriptan succinate oral tablet. The study consisted of a Screening Visit followed by Treatments A, B, C, D and E. Each of the treatment periods were separated by a 2 day washout period.

Mean skin erythema scores were also calculated for each of the patch treatments. Immediately after patch removal, mean scores were 1.40 or below for each of the four patch treatments. After 72 hours, the mean scores were each below 1.00.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. A method of treating a subject in need thereof, comprising:
 administering an effective amount of a triptan compound to a subject using an iontophoretic transdermal patch, wherein the patch comprises an anode reservoir and a cathode reservoir, wherein the anode reservoir comprises a polyamine hydrogel formed from a polyamine salt of a polyacrylate copolymer and an organic acid, and a gel forming amount of water;
 wherein the organic acid is a fatty acid, or a dicarboxylic acid, or a combination of both;
 wherein the polyamine hydrogel further comprises:
  about 3% to about 20% of a triptan compound in intimate mixture with the hydrogel; and
  optionally one or more additives,
 wherein the effective amount of the triptan compound is delivered to the subject within about one hour at an initial current between about 4 mA and about 5 mA without causing significant erythema.

2. The method of claim 1, wherein said effective amount is effective to treat a triptan compound responsive state.

3. The method of claim 2, wherein said triptan compound responsive state is a migraine.

4. The method of claim 1, wherein the hydrogel comprises at least about 80% water and about 3.0% to about 5.0% triptan compound.

5. The method of claim 1, wherein the hydrogel comprises between about 3% and about 10% polyamine salt.

6. The method of claim 1, wherein the hydrogel comprises between about 10% and about 18% polya mine salt.

7. The method of claim 1, wherein the polyamine salt is a salt of a methacrylate copolymer.

8. The method of claim 1, wherein the methacrylate copolymer is an alkylated methacrylate copolymer.

9. The method of claim 1, wherein the hydrogel comprises about 0.01% to about 1.0% antimicrobial agent.

10. The method of claim 1, wherein the organic acid comprises lauric acid, which is present in an amount between about 0.5% and about 7.0% .

11. The method of claim 1, wherein the organic acid comprises adipic acid, which is present in an amount between about 0.1% and about 2.0%.

12. The method of claim 1, wherein the triptan compound is almotriptan, frovatriptan, eletriptan, zolmitriptan, rizatriptan, sumatriptan, naratriptan, or a pharmaceutically acceptable salt thereof.

13. The method of claim 1, wherein the triptan compound is sumatriptan or a salt thereof.

14. The method of claim 1, wherein the triptan compound is sumatriptan succinate or sumatriptan hydrochloride.

15. The method of claim 1, wherein the patch is capable of administering an effective amount of the triptan compound without substantially affecting skin pH.

16. The method of claim 1, wherein the patch is capable of administering an effective amount of the triptan compound without substantially affecting skin temperature.

17. The method of claim 1, wherein the hydrogel has a pH of about 3 to about 8.

18. The method of claim 17, wherein the hydrogel has a pH of about 5.5 to about 7.

19. The method of claim 18, wherein the hydrogel has a pH of about 6.

20. The method of claim 1, wherein the anode reservoir further comprises a solubility enhancer, a permeation enhancer, an antimicrobial agent or any combination thereof.

21. The method of claim 1, wherein the patch comprises a battery which operates throughout use of the patch.

22. The method of claim 1, wherein the patch delivers a desired concentration of the triptan compound in less than one hour.

23. The method of claim 1, wherein the anode reservoir consists essentially of a polyamine hydrogel formed from:
 a polyamine salt of a polyacrylate copolymer and adipic acid, and
 a gel forming amount of water;
 wherein the polyamine hydrogel further comprises:
 between about 3% and about 10% of a triptan compound in intimate mixture with the hydrogel, and
 between about 0.05% and about 0.75% methyl para-hydroxy benzoate.

24. The method of claim 1, wherein the organic acid is a fatty acid, a dicarboxylic acid or a mixture thereof.

25. A method of treating a subject in need thereof, comprising administering an effective amount of sumatriptan or a salt thereof to a subject using an iontophoretic transdermal patch, wherein the patch comprises an anode reservoir and a cathode reservoir, wherein said anode reservoir comprises a polyamine hydrogel formed from:
 an alkylated methacrylate copolymer,
 at least about 80% water,
 between about 1.0% and about 5.0% lauric acid, and
 between about 0.05% and about 0.75% adipic acid; and
 wherein the polyamine hydrogel further comprises:
 between about 3% and about 10% sumatriptan or salt thereof in intimate mixture with the hydrogel, and
 between about 0.02% and about 0.5% methyl para-hydroxy benzoate; and
 wherein the effective amount of the triptan compound is delivered to the subject within about one hour at an initial current between about 4 mA and about 5 mA without causing significant erythema.

26. The method of claim 25, wherein sumatriptan or a salt thereof is sumatriptan succinate.

27. A method of treating a subject in need thereof, comprising administering an effective amount of sumatriptan succinate to a subject using an iontophoretic transdermal patch, wherein said patch comprises an anode reservoir and a cathode reservoir, wherein said anode reservoir comprises a polyamine hydrogel formed from:
 approximately 84% to about 88% water;
 approximately 4.0% to about 7.0% alkylated methacrylate co-polymer;
 approximately 1.0% to about 5.0% lauric acid; and
 approximately 0.05% to about 0.75% adipic acid;
 wherein the polyamine hydrogel further comprises:
 approximately 3.0% to about 5.0% sumatriptan succinate in intimate mixture with the hydrogel, and
 approximately 0.05% to about 0.75% methyl para-hydroxy benzoate; and wherein the effective amount of the triptan compound is delivered to the subject within about one hour at an initial current between about 4 mA and about 5 mA without causing significant erythema.

* * * * *

UNITED STATES PATENT AND TRADEMARK OFFICE
CERTIFICATE OF CORRECTION

PATENT NO.        : 8,366,600 B2                                    Page 1 of 1
APPLICATION NO.   : 12/214555
DATED             : February 5, 2013
INVENTOR(S)       : Sebree et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 344 days.

Signed and Sealed this
Eighteenth Day of November, 2014

Michelle K. Lee
*Deputy Director of the United States Patent and Trademark Office*